United States Patent [19]
Payne et al.

[11] Patent Number: 6,071,511
[45] Date of Patent: Jun. 6, 2000

[54] *BACILLUS THURINGIENSIS* ISOLATES, TOXINS, AND GENES SELECTIVELY ACTIVE AGAINST CERTAIN COLEOPTERAN PESTS

[75] Inventors: Jewel M. Payne, Davis; Tracy Ellis Michaels, Escondido; Gregory A. Bradfisch, San Diego; Judy Muller-Cohn, Del Mar; Jenny Fu, San Diego, all of Calif.

[73] Assignee: Mycogen Corporation, San Diego, Calif.

[21] Appl. No.: 09/100,437

[22] Filed: Jun. 19, 1998

Related U.S. Application Data

[60] Continuation-in-part of application No. 08/466,635, Jun. 6, 1995, Pat. No. 5,770,695, which is a division of application No. 08/101,863, Aug. 4, 1993, Pat. No. 5,427,786, which is a division of application No. 07/977,386, Nov. 11, 1992, abandoned, which is a division of application No. 07/771,964, Oct. 4, 1991, abandoned, and a continuation-in-part of application No. 08/611,928, Mar. 6, 1996, Pat. No. 5,824,792, which is a division of application No. 08/158,232, Nov. 24, 1993, Pat. No. 5,596,071, which is a continuation-in-part of application No. 07/887,980, May 22, 1992, abandoned.

[51] Int. Cl.$^7$ .............................. A01N 63/00; C12N 5/04; C12N 5/10
[52] U.S. Cl. ...................... 424/93.2; 435/419; 800/302; 536/23.7
[58] Field of Search .......................... 424/93.2; 435/419; 800/302; 514/12; 536/23.7

[56] References Cited

U.S. PATENT DOCUMENTS

| | | | |
|---|---|---|---|
| 4,797,276 | 1/1989 | Herrnstadt et al. | 424/89 |
| 4,849,217 | 7/1989 | Soares et al. | 424/93 |
| 4,853,331 | 8/1989 | Herrnstadt et al. | 435/252.1 |
| 4,910,016 | 3/1990 | Gaertner et al. | 424/93 |
| 4,966,765 | 10/1990 | Payne et al. | 424/93 |
| 5,024,837 | 6/1991 | Donovan et al. | 424/93 |
| 5,064,648 | 11/1991 | Hickle et al. | 424/93 |
| 5,208,017 | 5/1993 | Bradfisch et al. | 424/84 |
| 5,211,946 | 5/1993 | Payne et al. | 424/93 L |
| 5,260,058 | 11/1993 | Payne et al. | 424/93 L |
| 5,262,158 | 11/1993 | Payne e tla. | 424/93 L |
| 5,262,159 | 11/1993 | Payne et al. | 424/93 L |

FOREIGN PATENT DOCUMENTS

| | | |
|---|---|---|
| 0202739 | 11/1986 | European Pat. Off. . |
| 0337604 | 10/1989 | European Pat. Off. . |

OTHER PUBLICATIONS

Couch, T.L. (1980) "Mosquito Pathogenicity of *Bacillus thuringiensis* var. israelenis" Developments in Industrial Microbiology 22:61–67.

Beegle, C.C. (1978) "Use of Entomogenous Bacteria in Agroecosystems" Developments in Industrial Microbiology 20:97–104.

Krieg, V.A. et al. (1983) "*Bacillus thuringiensis* var. tenebrionis, a New Pathotype Effective Against Larvae of Coleoptera" Z. Ang. Ent. 96:500–508.

Herrnstadst, C. et al. (1986) "A New Strain of *Bacillus thuringiensis* with Activity Against Coleopteran Insects" Bio/Technology 4:305–308.

Klausner, A. (1984) "Microbial Insect Control" Bio/Technology pp. 408–416.

*Primary Examiner*—Robert A. Wax
*Assistant Examiner*—Devesh Srivastava
*Attorney, Agent, or Firm*—Saliwanchik, Lloyd & Saliwanchik

[57] ABSTRACT

The subject invention concerns *Bacillus thuringiensis* microbes with activity against select coleopteran pests, e.g., Diabrotica sp., Hypera sp., and various flea beetles. For example, the *B.t.* isolates of the invention are active against alfalfa weevils (AW, *Hypera brunneipennis*), rape flea beetles (RFB, *Phyllotreta cruciferae*), and corn rootworms (CRW, *Diabrotica undecimpunctata undecimpunctata*). Thus, these microbes can be used to control these pests. Further, genes encoding toxins active against these pests can be isolated from the *B.t.* isolates and used to transform other microbes. The transformed microbes then can be used to control susceptible coleopteran pests. In preferred embodiments, a gene from PS140E2 is used to transform plants so that the transformed plants are resistant to flea beetles of the genus Phyllotreta.

3 Claims, 2 Drawing Sheets

FIG. 1A

A. *Bacillus thuringiensis* PS28Q2
B. *Bacillus thuringiensis* PS45B1
C. *Bacillus thuringiensis* PS73J3
D. *Bacillus thuringiensis* PS75J1
E. *Bacillus thuringiensis* PS86A1
F. *Bacillus thuringiensis* PS86Q3
G. *Bacillus thuringiensis* PS92B
H. *Bacillus thuringiensis* PS140E2
I. *Bacillus thuringiensis* PS143J
J. *Bacillus thuringiensis* PS202U2

FIG. 1B

A. *Bacillus thuringiensis* PS74G1
B. *Bacillus thuringiensis* PS98A3
C. *Bacillus thuringiensis* PS101Z2

BACILLUS THURINGIENSIS ISOLATES, TOXINS, AND GENES SELECTIVELY ACTIVE AGAINST CERTAIN COLEOPTERAN PESTS

CROSS-REFERENCE TO A RELATED APPLICATION

The subject application is a continuation-in-part of U.S. patent application Ser. No. 08/466,635, filed Jun. 6, 1995 (now U.S. Pat. No. 5,770,695); which is a division of U.S. patent application Ser. No. 08/101,863, filed Aug. 4, 1993 (now U.S. Pat. No. 5,427,786); which is a division of U.S. patent application Ser. No. 07/977,386, filed Nov. 11, 1992 (now abandoned); which is a division of U.S. patent application Ser. No. 07/771,964, filed Oct. 4, 1991 (now abandoned).

The subject application is also a continuation-in-part of U.S. patent application Ser. No. 08/611,928, filed Mar. 6, 1996 (now U.S. Pat. No. 5,824,792); which is a division of U.S. patent application Ser. No. 08/158,232, filed Nov. 24, 1993 (now U.S. Pat. No. 5,596,071); which is a continuation-in-part of U.S. patent application Ser. No. 07/887,980, filed May 22, 1992 (now abandoned).

BACKGROUND OF THE INVENTION

*Bacillus thuringiensis* (*B.t.*) produces an insect toxin designated as δ-endotoxin. It is synthesized by the *B.t.* sporulating cell. The toxin, upon being ingested in its crystalline form by susceptible insect larvae, is transformed into biologically active moieties by the insect gut juice proteases. The primary target is insect cells of the gut epithelium, which are rapidly destroyed.

The reported activity spectrum of *B.t.* covers insect species within the order Lepidoptera, many of which are major pests in agriculture and forestry. The activity spectrum also includes the insect order Diptera, which includes mosquitos and black flies. See Couch, T. L. (1980) "Mosquito Pathogenicity of *Bacillus thuringiensis* var. *israelensis*," *Developments in Industrial Microbiology* 22:61–76; Beegle, C. C., (1978) "Use of Entomogenous Bacteria in Agroecosystems," *Developments in Industrial Microbiology* 20:97–104. Krieg et al. (1983) *Z. ang. Ent.* 96:500–508, describe a *B.t.* isolate named *Bacillus thuringiensis* var. *tenebrionis*, which is reportedly active against two beetles in the order Coleoptera. These are the Colorado potato beetle, *Leptinotarsa decemlineata*, and *Agelastica alni*.

In European Patent Application 0 202 739 there is disclosed a novel *B.t.* isolate active against Coleoptera. It is known as *B. thuringiensis* var. *san diego* (*B.t.sd.*). U.S. Pat. No. 4,966,765 discloses the coleopteran-active *Bacillus thuringiensis* isolate *B.t.* PS86B1. European Patent Application 0 337 604 also discloses a novel *B.t.* isolate active against Coleoptera. This isolate is *B.t.* PS43F. U.S. Pat. No. 5,596,071 discloses *B.t.* isolates PS86Q3, PS211B2, and PS140E2 as having activity against ants, as well as a clones containing toxin genes obtainable from these isolates.

Coleopteran-activestrains, such as *B.t.sd*, *B.t.* PS86B1, and *B.t.* PS43F, can be used to control foliar-feeding beetles. The Colorado potato beetle (*Leptinotarsa decemlineata*), for example, is susceptible to the delta-endotoxin of *B.t.sd*. and larvae are killed upon ingesting a sufficient dose of spore/crystal preparation on treated foliage.

There are a number of other beetles that cause economic damage. For example, Chrysomelid beetles such as Flea Beetles and Corn Rootworms and Curculionids such as Alfalfa Weevils are particularly important pests. Flea Beetles include a large number of small leaf feeding beetles that feed on the leaves of a number of grasses, cereals, and herbs. Flea Beetles include a large number of genera (e.g., Altica, Apphthona, Argopistes, Disonycha, Epitrix, Longitarsus, Prodagricomela, Systena, and Phyllotreta). The Flea Beetle *Phyllotreta crticiferae*, also known as the Rape or Canola Flea Beetle, is a particularly important pest. Other members of the genus Phyllotreta include *Phyllotreta striolata* and *Phyllotreta undulata*. *Psylliodes chrysocephala* is another type of flea beetle that is an important, biennial pest that attacks the stems and leaves of susceptible plants. Corn rootworms include species found in the genus Diabrotica (e.g., *D. undecimpunctata undecimpunctata, D. undecimpunctata howardii, D. longicornis, D. virgifera* and *D. balteata*). Corn rootworms cause extensive damage to corn and curcubits. The Western Spotted Cucumber Beetle, *D. undecimpunctata undecimpunctata*, is a pest of curcubits in the western U.S. Alfalfa weevils (also known as clover weevils) belong to the genus, Hypera (*H. postica, H. brunneipennis, H. nigrirostris, H. punctata* and *H. meles*), and are considered an important pest of legumes. The Egyptian alfalfa weevil, *H. brunneipennis*, is an important pest of alfalfa in the western U.S.

BRIEF SUMMARY OF THE INVENTION

The subject invention concerns *Bacillus thuringiensis* (*B.t.*) isolates which are active against Diabrotica sp., Hypera sp., and various genera of flea beetles, as listed above. For example, the *B.t.* isolates of the invention are active against alfalfa weevils (AW, *Hypera brunneipennis*), rape flea beetles (RFB, *Phyllotreta cruciferae*), and corn rootworms (CRW, *Diabrotica undecimpunctata undecimpunctata*). These activities were determined by tests as disclosed in Example 2.

The subject invention also includes mutants of the above *B.t.* isolates which have substantially the same pesticidal properties as the parent *B.t.* isolates. Procedures for making mutants are well known in the microbiological art. Ultraviolet light and nitrosoguanidine are used extensively toward this end.

Further, the invention also includes the treatment of substantially intact *B.t.* cells, and recombinant cells containing the gene of the invention, to prolong the pesticidal activity when the substantially intact cells are applied to the environment of a target pest. Such treatment can be by chemical or physical means, or a combination of chemical or physical means, so long as the technique does not deleteriously affect the properties of the pesticide, nor diminish the cellular capability in protecting the pesticide. The treated cell acts as a protective coating for the pesticidal toxin. The toxin becomes available to act as such upon ingestion by a target insect.

Still further, the invention includes the genes isolatable from the *B.t.* isolates which genes encode toxins (proteins) active against the above-noted pests. Specifically exemplified herein is a gene obtainable from a *B.t.* isolate designated PS140E2. This gene encodes a toxin designated 140E2 that, preferably, can be used to control pests of the genus Phyllotreta by in planta administration. The use of the toxin-encoding genes of the subject invention to control other pests, such as pests of the genus Psylliodes, is also contemplated.

BRIEF DESRIPTION OF THE DRAWINGS

FIG. 1—Photograph of a standard SDS polyacrylamide gel of *B.t.* isolates of the invention.

BRIEF DESCRIPTION OF THE SEQUENCES

SEQ ID NO. 1 is an N-terminal amino acid sequence for the 140E2 protein toxin.

SEQ ID NO. 2 is an oligonucleotide probe for the 140E2 gene.

DETAILED DISCLOSURE OF THE INVENTION

The *Bacillus thuringiensis* isolates of the subject invention have the following common characteristics in their biologically pure form:

Common Characteristics of *B.t.* Isolates of Invention

Colony morphology—Large colony, dull surface, typical *B.t.*

Vegetative cell morphology—typical *B.t.*

Culture methods—typical for *B.t.*

A comparison of the characteristics of the *B. thuringiensis* isolates of the invention to the characteristics of the known *B.t.* strains *B. thuringiensis* var. *san diego* (*B.t.sd*) and *B. thuringiensis* var. *kurstaki* (HD-1) is shown in Table 1.

TABLE 1

Comparison of B.t. Isolates Against B.t.sd. and B.t. HD-1

| Isolate | Type of Inclusion | Size of Alkalisoluble Proteins by SDS-PAGE |
|---|---|---|
| B.t. sd. | square wafer | 72, 64 kDa |
| B.t. HD-1 | bipyramid | 68, 130 kDa |
| B.t. PS92B | attached amorphic | 80 kDa |
| B.t. P573J3 | amorphic | 64, 75, 79, 81 kDa |
| B.t. P575J1 | amorphic | 63, 75, 79, 81 kDa |
| B.t. PS86A1 | multiple attached | 45, 58 kDa |
| B.t. PS86Q3 | 1 long and small amorphic | 58, 62, 98, 135, 155 kDa |
| B.t. PS28Q2 | 1 long and lemon | 63, 70 kDa |
| B.t. PS45B1 | multiple | 35, 135, 150 kDa |
| B.t. PS140E2 | multiple | 37, 70, 78 kDa |
| B.t. PS143J | amorphic | 29, 40, 78, 96, 98 kDa |
| B.t. PS202U2 | multiple long | 45, 58 kDa |
| B.t. PS74G1 | amorphic | 61, 115, 150, 155 kDa |
| B.t. PS98A3 | long | 33, 145, 155 kDa |
| B.t. PS101Z2 | long | 145, 160 kDa |

The cultures disclosed in this application have been deposited in the Agricultural Research Service Patent Culture Collection (NRRL), Northern Regional Research Center, 1815 North University Street, Peoria, Ill. 61604, U.S.A.

| Culture Deposit | Strain | Deposit Number | Deposit Date |
|---|---|---|---|
| *Bacillus thuringiensis* | PS92B | NRRL B-18889 | Sept. 23, 1991 |
| *Bacillus thuringiensis* | PS28Q2 | NRRL B-18888 | Sept. 19, 1991 |
| *Bacillus thuringiensis* | PS45B1 | NRRL B-18396 | August 16, 1988 |
| *Bacillus thuringiensis* | PS75J1 | NRRL B-18781 | March 7, 1991 |
| *Bacillus thuringiensis* | P586A1 | NRRL B-18400 | August 16, 1988 |
| *Bacillus thuringiensis* | PS86Q3 | NRRL B-18765 | February 6, 1991 |
| *Bacillus thuringiensis* | PS140E2 | NRRL B-18812 | April 23, 1991 |
| *Bacillus thuringiensis* | PS143J | NRRL B-18829 | May 31, 1991 |
| *Bacillus thuringiensis* | PS202U2 | NRRL B-18832 | May 31, 1991 |
| *Bacillus thuringiensis* | P574G1 | NRRL B-18397 | August 16, 1988 |
| *Bacillus thuringiensis* | PS98A3 | NRRL B-18401 | August 16, 1988 |
| *Bacillus thuringiensis* | PS101Z2 | NRRL B-18890 | October 1, 1991 |
| *E. coli* NM522 (Pmyc2367) (140E2) | | NRRL B-21149 | October 20, 1993 |
| B.t. MR513 (140E2) | | NRRL B-21914N | January 23, 1998 |

The subject cultures have been deposited under conditions that assure that access to the cultures will be available during the pendency of this patent application to one determined by the Commissioner of Patents and Trademarks to be entitled thereto under 37 CFR 1.14 and 35 U.S.C. 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit, and in any case, for a period of at least thirty (30) years after the date of deposit or for the enforceable life of any patent which may issue disclosing the cultures. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

The *B.t.* isolates of the invention can be cultured using standard art media and fermentation techniques. Upon completion of the fermentation cycle, the bacteria can be harvested by first separating the *B.t.* spores and crystals from the fermentation broth by means well known in the art. The recovered *B.t.* spores and crystals can be formulated into a wettable powder, liquid concentrate, granules, or other formulations by the addition of surfactants, dispersants, inert carriers and other components to facilitate handling and application for particular target pests. These formulation and application procedures are all well known in the art.

Formulated products can be sprayed or applied onto foliage to control phytophagous beetles or larvae.

Another approach that can be taken is to incorporate the spores and crystals of the *B.t.* isolates into bait granules containing an attractant and applying these granules to the soil for control of soil-inhabiting and foliage feeding Coleoptera. Formulated *B.t.* isolates can also be applied as a seed-coatin, or root treatment or total plant treatment.

The *B.t.* isolates cells can be treated prior to formulation to prolong the pesticidal activity when the cells are applied to the environment of a target pest. Such treatment can be by chemical or physical means, or by a combination of chemical and/or physical means, so long as the technique does not deleteriously affect the properties of the pesticide, nor diminish the cellular capability in protecting the pesticide. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as formaldehyde and glutaraldehyde; anti-infectives, such as zephiran chloride; alcohols, such as isopropyl and ethanol; various histologic fixatives, such as Bouin's fixative and Helly's fixative (See: Humason, Gretchen. L., Animal Tissue Techniques, W. H. Freeman and Company, 1967); or a combination of physical (heat) and chemical agents that prolong the activity of the toxin produced in the cell when the cell is applied to the environment of the target pest(s). Examples of physical means are short wavelength radiation such as gamma-radiation and X-radiation, freezing, UV irradiation, lyophilization, and the like.

Genes encoding toxins having activity against the target susceptible pests can be isolated from the *B.t.* isolates of the invention by use of well known procedures.

The toxin genes of the subject invention can be introduced into a wide variety of microbial hosts. Expression of the toxin gene results, directly or indirectly, in the intracellular production and maintenance of the pesticide. With suitable hosts, e.g., Pseudomonas, the microbes can be applied to the situs of coleopteran insects where they will proliferate and be ingested by the insects. The result is a control of the unwanted insects. Alternatively, the microbe hosting the toxin gene can be treated under conditions that prolong the activity of the toxin produced in the cell. The treated cell then can be applied to the environment of target pest(s). The resulting product retains the toxicity of the *B.t.* toxin.

Where the *B.t.* toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms,provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganismsinclude bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leitconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii;* and phytosphere yeast species such as *Rhodotorula rubra, R. glutinis, R. marina, R. aurantiaca, Cryptococcus albidus, C. diffluens, C. Iaurentii, Saccharomyces rose i, S. pretoriensis, S. cerevisiae, Sporobolomyces roseus, S. odorus, Kluyveromyces veronae,* and *Aureobasidium pollulans.* Of particular interest are the pigmented microorganisms.

A wide variety of ways are available for introducing the *B.t.* gene expressing the toxin into the microorganism host under conditions which allow for stable maintenance and expression of the gene. One can provide for DNA constructs which include the transcriptional and translational regulatory signals for expression of the toxin gene, the toxin gene under their regulatory control and a DNA sequence homologous with a sequence in the host organism, whereby integration will occur, and/or a replication system which is functional in the host, whereby integration or stable maintenance will occur.

The transcriptional initiation signals will include a promoter and a transcriptional initiation start site. In some instances, it may be desirable to provide for regulative expression of the toxin, where expression of the toxin will only occur after release into the environment. This can be achieved with operators or a region binding to an activator or enhancers, which are capable of induction upon a change in the physical or chemical environment of the microorganisms. For example, a temperature sensitive regulatory region may be employed, where the organisms may be grown up in the laboratory without expression of a toxin, but upon release into the environment, expression would begin. Other techniques may employ a specific nutrient medium in the laboratory, which inhibits the expression of the toxin, where the nutrient medium in the environment would allow for expression of the toxin. For translational initiation, a ribosomal binding site and an initiation codon will be present.

Various manipulations may be employed for enhancing the expression of the messenger, particularly by using an active promoter, as well as by employing sequences, which enhance the stability of the messenger RNA. The initiation and translational termination region will involve stop codon (s), a terminator region, and optionally, a polyadenylation signal.

In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiationcodon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the toxin expression construct during introduction of the DNA into the host.

By a marker is intended a structural gene which provides for selection of those hosts which have been modified or transformed. The marker will normally provide for selective advantage, for example, providing for biocide resistance, e.g, resistance to antibiotics or heavy metals; complementation, so as to provide prototropy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, e.g., siderophores, may be introduced into the host along with the structural gene expressing the toxin. In this manner, the enhanced expression of a siderophore may provide for a competitive advantage for the toxin-producinghost, so that it may effectively compete with the wild-type microorganisms and stably occupy a niche in the environment.

Where no functional replication system is present, the construct will also include a sequence of at least 50 basepairs (bp), preferably at least about 100 bp, and usually not more than about 1000 bp of a sequence homologous with a sequence in the host. In this way, the probability of legitimate recombination is enhanced, so that the gene will be integrated into the host and stably maintained by the host. Desirably, the toxin gene will be in close proximity to the gene providing for complementation as well as the gene providing for the competitive advantage. Therefore, in the event that a toxin gene is lost, the resulting organism will be likely to also lose the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the lambda left and right promoters, the tac promoter, the naturally-occurring promoters associated with the toxin gene, where functional in the host. See for example, U.S. Pat. Nos. 4,332,898, 4,342,832 and 4,356,270. The termination region may be the termination region normally associated with the transcriptional initiation region or a different transcriptional initiation region, so long as the two regions are compatible and functional in the host.

Where stable episomal maintenance or integration is desired, a plasmid will be employed which has a replication system which is functional in the host. The replication system may be derived from the chromosome, an episomal element normally present in the host or a different host, or a replication system from a virus which is stable in the host. A large number of plasmids are available, such as pBR322, pACYC184, RSF10100, pRO1614, and the like. See for example, Olson et al., (1982) J. Bacteriol. 150:6069, and Bagdasarian et al., (1981) Gene 16:237, and U.S. Pat. Nos. 4,356,270, 4,362,817, and 4,371,625.

The *B.t.* gene can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for finctioning in the ultimate host. In addition, one or more markers may be present, which have been described previously. Where integration is desired, the plasmid will desirably include a sequence homologous with the host oenome.

The transformants can be isolated in accordance with conventional ways, usually employing a selection technique, which allows for selection of the desired organism as against unmodified organisms or transferring organisms, when present. The transformants then can be tested for pesticidal activity.

Suitable host cells, where the pesticide-containingcells will be treated to prolong the activity of the toxin in the cell when the then treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts. of particular interest will be the prokaryotes and the lower eukaryotes, such as fungi. Illustrative prokaryotes, both Gram-negative and -positive, include Enterobacteriaceae, such as Escherichia, Erwinia, Shigeella, Salmonella, and Proteus; Bacillaceae; Rhizobiceae, such as Rhizobium; Spirillaceae, such as photobacterium, Zymomonas, Serratia, Aeromonas, Vibrio, Desitlfovibrio, Spirillum; Lactobacillaceae; Pseudomonadaceae, such as Pseudomonas and Acetobacter; Azotobacteraceae and Nitrobacteraceae. Among eukaryotesare fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Characteristics of particularinterest in selecting a host cell for purposes of production include ease of introducing the *B.t.* gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractivenessto pests for ingestion; ease of killing and fixing without damage to the toxin; and the like. Other considerations include ease of formulation and handling, economics, storage stability, and the like.

Host organisms of particular interest include yeast, such as Rhodotorula sp., Aureobasidiuim sp., Saccharomyces sp., and Sporobolomyces sp.; phylloplane organisms such as Pseudomonas sp., Erwinia sp. and Flavobacterium sp.; or such other organisms as Escherichia, Lactobacillus sp., Bacillus sp., Streptomyces sp., and the like. Specific organisms include *Pseudomonas aeruginosa, Pseudomonas fluorescens, Saccharomyces cerevisiae, Bacilluis thuringiensis, Escherichia coli, Bacillus subtilis, Streptomyces lividans,* and the like.

The cell will usually be intact and be substantially in the proliferative form when treated, rather than in a spore form, although in some instances spores may be employed.

Treatment of the recombinant microbial cell can be done as disclosed infra. The treated cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bio-availability or bioactivity of the toxin.

The cellular host containing the *B.t.* insecticidal gene may be grown in any convenient nutrient medium, where the DNA construct provides a selective advantage, providing for a selective medium so that substantially all or all of the cells retain the *B.t.* gene. These cells may then be harvested in accordance with conventional ways. Alternatively, the cells can be treated prior to harvesting.

The *B.t.* cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the coleopteran pest(s), e.g., plants, soil or water, by spraying, dusting, sprinkling, baiting, or the like.

All of the U.S. patents cited herein are hereby incorporated by reference.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing the B.t. Isolates of the Invention

A subculture of a B.t. isolate can be used to inoculate the following medium, a peptone, glucose, salts medium.

| Bacto Peptone | 7.5 g/l | |
|---|---|---|
| Glucose | 1.0 g/l | |
| $KH_2PO_4$ | 3.4 g/l | |
| $K_2HPO_4$ | 4.35 g/l | |
| Salt Solution | 5.0 ml/l | |
| $CaCl_2$ Solution | 5.0 ml/l | |
| Salts Solution (100 ml) | | |
| $MgSO_4 \cdot 7H_2O$ | 2.46 g | |
| $MnSO_4 \cdot H_2O$ | 0.04 g | |
| $ZnSO_4 \cdot 7H_2O$ | 0.28 g | |
| $FeSO_4 \cdot 7H_2O$ | 0.40 g | |
| $CaCl_2$ Solution (100 ml) | | |
| $CaCl_2 \cdot 2H_2O$ | 3.66 g | pH 7.2 |

The salts solution and $CaCl_2$ solution are filter-sterilizedand added to the autoclaved and cooked broth at the time of inoculation. Flasks are incubated at 30° C. on a rotary shaker at 200 rpm for 64 hr.

The above procedure can be readily scaled up to large ferrnentors by procedures well known in the art.

The B.t. spores and crystals, obtained in the above fermentation, can be isolated by procedures well known in the art. A frequently-used procedure is to subject the harvested fermentation broth to separation techniques, e.g., centrifugation.

EXAMPLE 2

Testing of B.t. Isolates, Spores, and Toxin Crystals Against the Rape Flea Beetle, Eavptian Alfalfa Weevil, and Western Spotted Cucumber Beetle B.t isolates of the subject invention were tested against the Rape Flea beetle (*Phyllotreta cruciferae*) as follows:

Leaf sections were dipped into a suspension containing the B.t. isolate and allowed to dry. Adult beetles were placed in plastic cups, and the leaf section was placed between the cup rim and the cardboard lid. Cups were inverted and held on moist blotter paper at room temperature. Four days after treatment the amount of leaf feeding damage was recorded.

B.t. isolates of the subject invention were also tested against the Egyptian alfalfa weevil (*Hypera brunneipennis*) as follows:

A suspension of the B.t. preparation was pipetted onto the surface of a 1.5% agar diet in a 24 well assay tray. When it was completely dry, one, second instar, larvae was placed in each well. A sheet of Mylar was heat sealed over the tray and pierced with pins, and the tray was held at 25° C. for six days before mortality was determined.

B.t. isolates of the subject invention were further tested against the Western Spotted Cucumber Beetle (*Diabrotica undecimpunctata undecimpunctata*) as follows:

Approximately 1 ml of 1.5% agar diet was added to each well of an assay plate. The surface of the diet was treated with a B.t. suspension, allowed to dry then infested with up to 5 larvae per well before the tray was sealed with ventilated Mylar. Mortality was determined at intervals, and a larval weight or instar determination was finally made on day 10.

EXAMPLE 3

Purification and N-Terminal Sequencing of B.t. Isolate PS140E2

B.t. isolate PS140E2 was grown as described in Example 1. Sporulated cultures were harvested by standard sedimentation centrifugation. Parasporal protein inclusions were partially purified by sodium bromide (26–40%) isopycnic gradient centrifugation (Pfannenstiel, M. A., E. J. Ross, V. C. Kramer, and K. W. Nickerson [1984] FEMS Microbiol. Lett. 21:39). Fractions containing the parasporal inclusions were electrophoresed on denaturing polyacrylamide gels, peptides were bound to PVDF membrane (Millipore, Bedford, Mass.) by western blotting techniques (Towbin, H., T. Staehelin, and K. Gordon [1979] Proc. Natl. Acad. Sci. U.S.A. 76:4350) and the N-terminal amino acids were determined by the standard Edman reaction with an automated gas-phase sequenator (Hunkapiller, M. W., R. M. Hewick, W. L. Dreyer, and L. E. Hood [1983] Meth. Enzymol. 91:399).

The following N-terminal amino acid sequence (SEQ ID NO. 1) was obtained from a predominant, approximately 35 kDa polypeptide present in the parasporal inclusion preparation:

ANTTQSFHFSNILDYK (amino acid abbreviations are according to standard IUPAC conventions). From this sequence data oligonucleotideprobes were synthesized on an Applied Biosystems, Inc. DNA synthesis machine.

EXAMPLE 4

Molecular Cloning and Expression of a Novel Toxin Gene from *Bacillus thuringiensis* Strain PS140E2

Total cellular DNA was prepared from B.t. PS140E2 cells grown to an optical density, at 600 nm, of 1.0. Cells were pelleted by centrifugation and resuspended in protoplast buffer (20 mg/ml lysozyme in 0.3M sucrose, 25 mM Tris-Cl [pH 8.0], 25 mM EDTA). After incubation at 37° C. for 1 hour, protoplasts were lysed by two cycles of freezing and thawing. Nine volumes of a solution of 0.1 M NaCl, 0.1% SDS, 0.1 M Tris-Cl were added to complete lysis. The cleared lysate was extracted twice with phenol:chloroform (1:1). Nucleic acids were precipitated with two volumes of ethanol and pelleted by centrifugation. The pellet was resuspended in TE buffer and RNase was added to a final concentration of 50 g/ml. After incubation at 37° C. for 1 hour, the solution was extracted once each with phenol:chloroform (1:1) and TE-saturated chloroform. DNA was precipitated from the aqueous phase by the addition of one-tenth volume of 3M NaOAc and two volumes of ethanol. DNA was pelleted by centrifugation, washed with 70% ethanol, dried, and resuspended in TE buffer.

A gene library was constructed from PS 140E2 DNA partially digested with NdeII. Partial restriction digests were fractionated by agarose gel electrophoresis. DNA fragments 9.3 to 23 kbp in size were excised from the gel, electroeluted from the gel slice, purified on an Elutip-D ion exchange column (Schleicher and Schuell, Keene, N.H.), and recovered by ethanol precipitation. The NdeII inserts were ligated into BamHI-digested LambdaGem-11 (Promega, Madison, Wis.). Recombinantphage were packaged and plated on *E. coli* KW251 cells. Plaques were screened by hybridizationto an oligonucleotideprobe deduced from the amino acid sequence of the PS140E2 35 kDa toxin. The sequence of this probe (SEQ ID NO. 2) was:

5' TTT CAT TTT TCW AAT ATT TTA GAT TAT AAA 3' wherein W=A or T, according to standard IUPAC conventions. Hybridizing phage were plaque-purified and used to infect liquid cultures of *E. coli* KW25 1 cells for isolation of DNA by standard procedures (Maniatis, et al.).

For subcloning the gene encoding the approximately 35 kDa PS 140E2 polypeptide, preparative amounts of phage DNA were digested with SalI and electrophoresed on an agarose gel. The approximately 13.5 kbp band containing the toxin gene was excised from the gel, electroeluted from the gel slice, and purified by ion exchange chromatography as described above. The purified DNA insert was ligated into XhoI-digested pHTBlueII (an *E. coli/B. thuringiensis* shuttle vector comprised of pBluescript S/K [Stratagene, La Jolla, Calif.] and the replication origin from a resident *B.t.* plasmid [D. Lereclus et al. 1989. FEMS Microbiology Letters 60:211–218]). The ligation mix was used to transform frozen, competent *E. coli* NM522 cells (ATCC 47000).

β-galactosidase-negative transformants were screened by restriction digestion of alkaline lysate plasmid minipreps as above. The desired plasmid construct, pMYC2367, contains a toxin gene. A subculture of *E. coli* NM522 containing plasmid pMYC2367 was deposited in the permanent collection of the Patent Culture Collection (NRRL), Regional Research Center, 1815 North University Street, Peoria, Ill. 61604 U.S.A. on Oct. 20, 1993. The accession number is NRRL B-21149.

pMYC2367 was introduced into the acrystalliferous (Cry-) *B.t.* host, CryB (A. Aronson, Purdue University, West Lafayette, Ind.), by electroporation. The resulting strain was designated MR513. Expression of polypeptides approximately 35 kDa and 80 kDa in sporulated cultures of MR513 were demonstrated by SDS-PAGE analysis and western 5 blotting.

EXAMPLE 5

Additional Bioassays of PS28Q2, PS140E2, and MR513 Against Phyllotreta

The pesticidal activity of strains PS140E2, PS28Q2, and MR513 (a clone, derived from PS140E2, which expresses the exemplified 140E2 toxin gene) were further evaluated as follows. Wild *Phyllotreta cruciferae* were collected and held in rearing chambers at 25° C., 16L:8D photoperiod. Five canola (Hyola 401) seeds were planted in standard potting soil. Cotyledons were excised from seedlings and dipped in *B.t.* suspensions (100 ug toxin/ml) made with 0.1% Bond (Bond served as a sticking agent). A single treated cotyledon was allowed to dry and was placed in a plastic well (NuTrend trays) containing approximately 1 ml of a 2% agar gel. The agar gel served as a moisture source to increase the longevity of the excised cotyledons. A single adult beetle was placed in each assay well. Assays were stored at room temperature. Mortality and plant damage was assessed at 4 and 7 days post treatment. Cotyledon damage was assessed on a 1–10 point scale with a scoring of 10 corresponding to complete destruction of plant tissue.

Strains PS140E2. PS28Q2, and MR513 exhibited excellent activity against the Phylloireta pests. Several treatments showed reduced plant damage relative to untreated and CryB (a crystal-minus *B.t.* strain) controls.

EXAMPLE 6

Insertion of Toxin Gene Into Plants

One aspect of the subject invention is the transformation of plants with genes encoding the insecticidal toxin of the present invention. The transformed plants are resistant to attack by the target pest. Preferred genes will be stably maintained and expressed at high levels in the transformed plant and/or plant cells.

Genes encoding pesticidal toxins, as disclosed herein, can be inserted into plant cells using a variety of techniques which are well known in the art. For example, the novel genes coding for the novel insecticidal toxins, as disclosed herein, can be inserted into plant cells using the Ti plasmid from *Agrobacter tumefaciens*. Plant cells can then be caused to regenerate into plants (Zambryski, P., Joos, H., Gentello, C., Leemans, J., Van Montague, M. and Schell, J [1983] *Cell* 32:1033–1043). A particularly useful vector in this regard is pEND4K (Klee, H. J., Yanofsky, M. F. and Nester, E. W. [1985] *Bio/Technology* 3:637–642). This plasmid can replicate both in plant cells and in bacteria and has multiple cloning sites for passenger genes. A toxin gene, for example, can be inserted into the BamHI site of pEND4K, propagated in *E. coli*, and transformed into appropriate plant cells.

A large number of cloning vectors comprising a replication system in *E. coli* and a marker that permits selection of the transformed cells are available for preparation for the insertion of foreign genes into higher plants. The vectors comprise, for example, pBR322, pUC series, M13mp series, pACYC184, etc. Accordingly, the sequence encoding the Bacillus toxin can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecularbiological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant. other DNA sequences may be necessary. If, for example, the Ti or Ri plasmid is used for the transformation of the plant cell. then at least the right border, but often the right and the left border of the Ti or Ri plasmid T-DNA, has to be joined as the flanking region of the genes to be inserted.

The use of T-DNA for the transformation of plant cells has been intensively researched and sufficiently described in EP 120 516; Hoekema (1985) In: *The Binary Plant Vector System,* Offset-durkkerij Kanters B. V., Alblasserdam, Chapter 5; Fraley et al., *Crit. Rev. Plant Sci.* 4:1–46; and An et al. (1985) *EMBO J.* 4:277–287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobacterium rhizogenes* as transformationagent, fusion, injection, biolistics (microparticle bombardment), or electroporation as well as other possible methods. If Agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in Agrobacteria. The intermediate vector can be transferred into *Agrobacterium tumefaciens* by means of a helper plasmid (conjugation). Binary vectors can replicate themselves both in *E. coli* and in Agrobacteria. They comprise a selection marker gene and a linker or polylinker which are framed by the right and left T-DNA border regions. They can be transformed directly into Agrobacteria (Holsters et al. [1978] *Mol. Gen. Genet.* 163:181–187). The Agrobacterium used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterizim tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives. In biolistic transformation, plasmid DNA or linear DNA can be employed.

The transformed cells are regenerated into morphologicallynormal plants in the usual manner. If a transformation event involves a germ line cell, then the inserted DNA and corresponding phenotypic trait(s) will be transmitted to progeny plants. Such plants can be grown in the normal manner and crossed with plants that have the same transformed hereditary factors or other hereditary factors. The resulting hybrid individuals have the corresponding phenotypic properties.

In a preferred embodiment of the subject invention, plants will be transformed with genes wherein the codon usage has been optimized for plants. See, for example, U.S. Pat. No. 5,380,831. Also, advantageously, plants encoding a truncated toxin will be used. The truncated toxin typically will encode about 55% to about 80% of the full length toxin. Methods for creating synthetic Bacillus genes for use in plants are known in the art.

EXAMPLE 7

Cloning of Novel *B. thuringiensis* Gene Into Baculoviruses

The novel genes of the invention can be cloned into baculoviruses such as *Azitographa californica* nuclearpolyhedrosis virus (AcNPV). Plasmids can be constructed that contain the AcNPV genome cloned into a commercial cloning vector such as pUC8. The AcNPV genome is modified so that the coding region of the polyhedrin gene is removed and a unique cloning site for a passenger gene is placed directly behind the polyhedrin promoter. Examples of such vectors are pGP-B6874, described by Pennock et al. (Pennock, G. D., Shoemaker, C. and Miller, L. K. [1984] *Mol. Cell. Biol.* 4:399–406), and pAC380, described by Smith et al. (Smith, G. E., Summers, M. D. and Fraser, M. J. [1983] *Mol Cell. Biol.* 3:2156–2165). The gene coding for the novel protein toxin of the invention can be modified with BamHI linkers at appropriate regions both upstream and downstream from the coding region and inserted into the passenger site of one of the AcNPV vectors.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A method for controlling a coleopteran pest selected from the group consisting of the genera IIypera, Diabrotica, Phyllotreta, Altica, Apphthona, Argopistes, Disonycha. Epitrix, Longitarsus, Prodagricomela, and Systena which comprises contacting said pest with toxin expressed by a host transformed with a gene that encoeds a toxin from a *Bacillus thuringiensis* isolate designated PS140E2.

2. The method according to claim 1, wherein said host is a plant cell.

3. The method according to claim 1, wherein said host is a plant.

* * * * *

UNITED STATES PATENT AND TRADEMARK OFFICE
CERTIFICATE OF CORRECTION

PATENT NO. : 6,071,511
DATED : June 6, 2000
INVENTOR(S) : Payne et al.

Page 1 of 3

It is certified that error appears in the above-identified patent and that said Letters Patent is hereby corrected as shown below:

Title page,
Item [60], line 4, "Nov. 11, 1992" should read -- Nov. 17, 1992 --.

Column 1,
Line 59, "Coleopteran-activestrains," should read -- Coleopteran-active stains, --.

Column 2,
Line 7, "*Phyllotreta crticiferae*," should read -- *Phyllotreta cruciferae*, --.

Column 3, Table 1,
Line 4, "P573J3" should read -- PS73J3 --.
Line 5, "P575J1" should read -- PS75J1 --.

Column 3,
Line 55, "P586A1" should read -- PS86A1 --.
Line 58, "P574G1" should read -- P574G1 --.

Column 4,
Line 39, "ofsoil-inhabitingand" should read -- of soil-inhabiting and --.
Line 41, "seed-coatin," should read -- seed-coating --.
Line 61, "thetarget pest(s)." should read -- the target pest(s). --.

Column 5,
Line 22, "microorganisms,provide" should read -- microorganisms, provide --.
Line 29, "microorganismsinclude" should read -- microorganisms include --.
Line 35, "Leitconostoc," should read -- *Leuconostoc*, --.
Line 47, "*Saccharomyces rose i*," should read -- *Saccharomyces rosei*, --.

Column 6,
Lines 16-17, "codon (s)," should read -- codon(s), --.
Line 50, "toxin-producinghost," should read -- toxin-producing host, --.

Column 7,
Line 21, "RSF10100," should read -- RSF1010, --.
Line 33, "finctioning" should read -- functioning --.
Line 37, "host oenome." should read -- host genome. --.
Line 57, "Shigeella," should read -- *Shigella*, --.
Line 60, "Desitlfovibrio," should read -- *Desulfovibrio*, --.
Line 63, "eukaryotesare fungi," should read -- eukaryotes are fungi, --.

UNITED STATES PATENT AND TRADEMARK OFFICE
CERTIFICATE OF CORRECTION

PATENT NO.   : 6,071,511
DATED        : June 6, 2000
INVENTOR(S)  : Payne et al.

It is certified that error appears in the above-identified patent and that said Letters Patent is hereby corrected as shown below:

Column 8,
Line 1, "particularinterest in" should read -- particular interest in --.
Line 10, "attractivenessto pests" should read -- attrativeness to pests --.
Line 15, "Aureobasidiuim sp.," should read -- *Aureobasidium* sp., --.

Column 9,
Lines 34-35, "filter-sterilizedand" should read -- filter-sterilized and --.
Line 39, "ferrnentors" should read -- fermentors --.
Line 48, "Eavptian Alfalfa" should read -- Egyptian Alfalfa --.

Column 10,
Line 56, "Iysis." should read -- lysis. --.

Column 11,
Line 9, "Recombinantphage" should read -- Recombinant phage --.
Line 10, "hybridizationto" should read -- hybridization to --.
Line 11, "oligonucleotideprobe" should read -- oligonucleotide probe --.
Line 19, "KW25 1 cells" should read -- KW251 cells --.
Line 23, "SaII" should read -- *Sal*I --.

Column 12,
Line 7, "Phylloireta pests." should read -- *Phyllotreta* pests. --.

Column 13,
Line 34, "*Agrobacterizim*" should read -- *Agrobacterium* --.

Column 14,
Lines 1-2, "morphologicallynormal" should read -- morphologically normal --.
Line 25, "*Azitographa*" should read -- *Autographa* --.
Lines 25-26, "nuclearpolyhedrosis" should read -- nuclear polyhedrosis --.

UNITED STATES PATENT AND TRADEMARK OFFICE
CERTIFICATE OF CORRECTION

PATENT NO. : 6,071,511
DATED : June 6, 2000
INVENTOR(S) : Payne et al.

It is certified that error appears in the above-identified patent and that said Letters Patent is hereby corrected as shown below:

Column 15,
Line 22, "Iiypera," should read -- *Hypera* --.

Signed and Sealed this

Fifteenth Day of January, 2002

Attest:

JAMES E. ROGAN
*Director of the United States Patent and Trademark Office*

*Attesting Officer*

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 16 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:1:

-continued

```
Ala Asn Thr Thr Gln Ser Phe His Phe Ser Asn Ile Leu Asp Tyr Lys
1               5                   10                  15
```

(2) INFORMATION FOR SEQ ID NO:2:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

TTTCATTTTT CWAATATTTT AGATTATAAA                        30